United States Patent [19]
Collins et al.

[11] Patent Number: 5,705,724
[45] Date of Patent: Jan. 6, 1998

[54] AROMATICS ALKYLATION WITH CRACKED RECYCLED PLASTICS

[75] Inventors: Nick A. Collins, Medford; Larry A. Green, Mickleton; Anagha A. Gupte, Marlton; David O. Marler, Deptford; William J. Tracy, III, Sewell, all of N.J.

[73] Assignee: Mobil Oil Corporation, Fairfax, Va.

[21] Appl. No.: 548,850

[22] Filed: Oct. 26, 1995

[51] Int. Cl.$^6$ .................................................. C07C 2/66
[52] U.S. Cl. .................. 585/446; 585/241; 585/455; 585/456; 585/464; 585/465; 585/466; 585/467
[58] Field of Search ........................ 585/241, 446, 585/455, 456, 459, 462, 464, 466, 467, 465

[56] References Cited

U.S. PATENT DOCUMENTS

| | | | |
|---|---|---|---|
| 2,994,679 | 8/1961 | Jones et al. | 585/241 |
| 4,108,730 | 8/1978 | Chen | 201/2.5 |
| 4,118,281 | 10/1978 | Yan | 201/2.5 |
| 5,053,573 | 10/1991 | Jorgensen et al. | 585/475 |
| 5,191,134 | 3/1993 | Le | 585/446 |
| 5,491,270 | 2/1996 | Chin et al. | 585/467 |

OTHER PUBLICATIONS

Effects of Polyolefins on Thermal Cracking of Heavy Crude by M. Stanciulescu.
Studies on the Use of Untreated Easte Plastics in Thermal Cracking of Vacuum Reside by M. Gebauer, et al.

Primary Examiner—Glenn Caldarola
Assistant Examiner—Bekir L. Yildirim
Attorney, Agent, or Firm—Malcolm D. Keen; Gerald L. Harris

[57] ABSTRACT

A process is disclosed for the production of alkylaromatic compounds employing olefinic liquid from thermally or catalytically cracked plastics as alkylating agent. The process comprises contacting a feedstream comprising alkylatable aromatics and the olefinic liquid with acidic alkylation catalyst under alkylation conditions in an alkylation zone; and recovering an effluent stream comprising alkylaromatic compounds. The alkylation can be performed with the product of plastics pyrolysis or with non-degraded plastic feedstock in-situ with thermal/catalytic degradation of the plastic.

18 Claims, No Drawings

AROMATICS ALKYLATION WITH CRACKED RECYCLED PLASTICS

FIELD OF THE INVENTION

This invention relates to a novel process for the disposal of plastic waste material. The invention especially relates to a process for the disposal of olefinic cracked plastic material by utilizing the catalytically or thermally cracked plastic as alkylating agent for aromatics alkylation individually, in combination with other chemicals or as contained in a petroleum refinery stream.

BACKGROUND OF THE INVENTION

Where once material recycling and resource recovery were common words and practice in but a few industries, in a surprisingly short time they are now common in virtually every home and industry in the land. Responding to the new awareness of the fragility of our ecosystem with passion and prudence, society has set about the rectification of past material excesses by falling upon the more ubiquitous materials used in modern civilization for corrective recovery. There is none more ubiquitous than plastics and no more ubiquitous plastics than polyethylene and polypropylene.

Most plastic materials are produced from petroleum derived raw materials. Petroleum derived hydrocarbons are the main component of petroleum derived fuels and petrochemicals. There have been many attempts made in the past to convert all sorts of waste materials into petroleum type products, either fuels, lubricating oils, coke, or other products. In U.S. Pat. No. 1,950,811 there is disclosed a process for recovering oil and coke from oil bearing residues in combination with non-petroleum raw materials such as coal, peat or sawdust by treating a suitable feed at high temperatures of about 900° to 1,000° F. In U.S. Pat. No. 2,412,879, a process for producing coke is disclosed wherein the feed to the coker is a mixture of conventional petroleum based coker feed and about 1–10% cellulosic material.

In U.S. Pat. No. 3,909,364, a carbonizable waste, such as garbage and sanitary sludge, is mixed with coal. This mixture is then devolatilized to produce a char which is mixed with residual oil to produce a solid fuel product.

None of these prior processes has taken into account or been designed to treat plastic waste materials. Pyrolysis processes have been described as offering the possibility of conversion of some solid organic wastes. Reference is here made and incorporated by reference to "Industrial Solid Wastes Management", pp 356–406, Proceedings of the National Industrial, Solid Wastes Management Conference, for a discussion of some of the conventional means for carrying out this desirable work. Pyrolysis of plastics is also the objective of a joint-industry program on plastics pyrolysis. Pyrolyzed plastics are produced through the program and the pyrolyzed product is available for utilization studies.

In U.S. Pat. No. 4,108,730, there is disclosed a means for disposing of solid polymeric wastes, such as rubber tires, plastic wares, plastic packaging, scrap plastic, etc. The process dissolves these materials in heavy petroleum oils such as FCC heavy cycle oil in the absence of added hydrogen. The feeds are dispersed and dissolved with little or no gas evolution. The resultant liquid is said to resemble crude oil and to make an excellent feed to a catalytic cracker. The cracking of this feed results in the usual array of products from a cat cracker.

In U.S. Pat. No. 4,118,281, a process has been disclosed for the dissolution of organic waste materials, including garbage, plastic, paper, wood, rubber, etc. in a conventional feed to a delayed coker unit process. Thermal decomposition of this mixture under conventional coker operating conditions is said to convert this feed into oil, water, gases and coke. The waste material which is being used to augment the conventional coker feed is suitably dissolved in a refinery fraction such as catalytic cracker recycle, FCC main column bottoms, TCC syntower bottoms, and the like. The preferred dissolving materials for these wastes are set forth to be fresh or recycle petroleum coker feed. This patent holds that carrying out the process described therein produces more oil than gas phase pyrolysis of organic waste materials.

As noted above, the high conversion petroleum refining processes of fluid catalytic cracking and coking have been adapted as means to dispose of plastic materials conjointedly with hydrocarbon processing. Plastics pyrolysis has been successfully achieved to produce a pyrolyzed plastic liquid product that is rich in olefins and aromatics. The challenge to the artisan is to find methods to utilize these pyrolyzed plastic stream that are practical and economically advantageous.

It is an objective of the present invention to develop processes for upgrading the liquid product obtained from plastic pyrolysis into higher value, commercial material.

A specific objective of the present invention is to provide methods to employ liquid pyrolyzed plastic streams as aromatics alkylating agents for a variety of aromatics rich streams found in the basic chemical and petroleum industries so that these waste plastics may, in effect, be returned to commerce as high value materials.

SUMMARY OF THE INVENTION

Pyrolyzed plastics have been found to be a very useful source of olefins for alkylation of various types of mononuclear and polynuclear aromatics individually and separately or as contained in a petroleum refinery stream. Alkylation, it has been discovered, proceeds with typical acidic aromatics alkylation catalysis but has been found to be particularly rewarding when alkylation is carried out in contact with solid metallosilicate catalyst particles. It has been found that the total liquid product (TLP) of plastics pyrolysis can be employed as alkylating agent or portions of the TLP containing a preponderance of higher boiling, non-aromatic olefins can be successfully utilized to prepare alkylated aromatic for automatic transmission fluid (ATF), linear alkyl benzenes (LABs) for detergents, and the like.

More particularly, a process has been discovered for the production of alkylaromatic compounds employing olefinic liquid from thermally or catalytically cracked plastics as alkylating agent. The process comprises contacting a feedstream comprising alkylatable aromatics and the olefinic liquid with acidic alkylation catalyst under alkylation conditions in an alkylation zone; and recovering an effluent stream comprising alkylaromatic compounds.

The process alkylation catalyst is selected from Lewis acids such as HF, $H_2SO_4$, $AlCl_3$, $BF_3$, $FeCl_3$, $TiCl_4$, $ZnCl_2$ and $P_2O_5$. Also, effective catalyst are selected from acidic layered clays, acidic natural or synthetic zeolites and mixed metal oxide super acids. Mixed metal oxide super acids are described in M. Hino and K. Arata, J. Chem. Soc. Chem. Commun., 1987, 1259; and K. Arata and M. Hino, Proc. 9th Int. Cong. on Catal., 1988, 4, 1727.

The effective zeolite catalysts include ZSM-5, ZSM-11, ZSM-12, ZSM-23, ZSM-35, and ZSM-48, ZSM-50, Zeolite Beta, MCM-56, MCM-22, MCM-36, MCM-49, ultrastable zeolite Y (USY), zeolite X, TMA Offretite, TEA Mordenite, Clinoptilolite, Mordenite, rare earth-exchanged zeolite Y (REY), Amorphous Silica-Alumina and Dealuminized Y. Catalysts also include mixed metal oxide superacids and acidified clays.

Useful alkylatable aromatics for the process comprise alkylatable aromatics in a petroleum refinery stream especially lube oil raffinate and extracts, catalytic or thermal crackate and light cycle oil. However, apart from refinery streams, aromatics such as benzenes and naphthalenes may be alkylated by the process of the invention.

DETAILED DESCRIPTION OF THE INVENTION

Aromatics alkylation is a key step in the manufacture of several products in the chemical industry such as linear alkyl benzenes (LABS) for detergents. It is also of importance in the fuels component of the petroleum refining industry in processes such as the alkylation of light cycle oil (LCO) to improve cetane index for use as diesel fuel. Another important process in the lubes component of the petroleum industry is the alkylation of lube extracts from solvent refined neutral distillates. Alkylation of the extracts has the potential to lower their mutagenicity index (MI) and upgrade them to higher value streams. In addition, there is a growing environmental pressure for conversion of scrap plastics into usable products in a safe and effective manner.

This invention teaches a process for alkylation of aromatics with the olefins generated from thermal or catalytic degradation of scrap plastics. Alkylation is carried out in the presence of conventional acidic alkylation catalyst but preferably in the presence of solid acid catalysts such as acidified clay, mixed metal oxide superacids such as $WO_x/ZrO_2$ or zeolites such as USY and MCM-56. The use of olefins generated from degradation of scrap plastics for the alkylation of aromatics not only provides a lower cost alternative to existing olefin sources but also has the potential for generating products with unique properties. The process provides a low cost, environmentally friendly method to recycle scrap plastics to higher-value products.

Preferably, the process of the invention is carried out using the product of a prior process for pyrolysis or degradation of plastics where the pyrolyzed product contains the olefins that are effective as alkylating agent. However, another approach to alkylation is to conduct the alkylation in-situ concurrent with the thermal or catalytic degration of the plastic materials. Indeed, predegraded or non-degraded plastic materials can be used directly as feedstock for alkylation under conditions that produce the requisite alkylating agent in the presence of alkylatable aromatics.

The selection of thermally or catalytically cracked or pyrolyzed plastics useful in the process of the invention is not limited to those degraded plastics produced by but one specific process. The artisan knows well that there is a plethora of cracking processes and conditions that can produce the olefinic alkylating agent from plastics useful in the present invention. Some plastics cracking processes may be superior but the production of the olefinic alkylating agent is the only paramount criterion for selection of the cracking product from a process useful in the invention. However, it is preferred, but not restricted, that the crackate be produced from high or low density polyethylene, polypropylene, polystyrene or mixtures thereof.

Catalysts useful in the present invention include the more conventional Lewis acid type catalysts known to be effective in alkylation of aromatics. These include HF, $H_2SO_4$, $AlCl_3$, $BF_3$, $FeCl_3$, $TiCl_4$, $ZnCl_2$ and $P_2O_5$, and the like.

Catalysts preferred for use herein include the crystalline aluminosilicate zeolites having a silica to alumina ratio of at least 12, a constraint index of about 1 to 12 and acid cracking activity greater than 120. Acid cracking activity (alpha value or alpha number) is a measure of zeolite acidic functionality and is more fully described together with details of its measurement in U.S. Pat. No. 4,016,218, *J. Catalysis*, 6, pp. 278–287 (1966) and *J. Catalysis*, 61, pp. 390–396 (1980).

Representative of the ZSM-5 type zeolites are ZSM-5, ZSM-11, ZSM-12, ZSM-23, ZSM-35, ZSM-48. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,842 for ZSM-23; U.S. Pat. No. 4,016,245 for ZSM-35.

A preferred catalyst for use in the present invention is MCM-56. MCM-56 is a member of the MCM-22 group useful in the invention which includes MCM-22, MCM-36, MCM-49 and MCM-56. MCM-22 is described in U.S. Pat. No. 4,954,325. MCM-36 is described in U.S. Pat. No. 5,250,277 and MCM-36 (bound) is described in U.S. Pat. No. 5,292,698. MCM-49 is described in U.S. Pat. No. 5,236,575 and MCM-56 is described in U.S. Pat. No. 5,362,697.

In general, the useful zeolite catalysts embrace two categories of zeolite, namely, the intermediate pore size variety as represented, for example, by ZSM-5, which possess a Constraint Index of greater than about 2 and the large pore variety as represented, for example, by zeolites Y and Beta, which possess a Constraint index no greater than about 2. Both varieties of zeolites will possess a framework silica-to-alumina ratio of greater than about 7. The method by which Constraint Index is determined is described fully in U.S. Pat. No. 4,016,218, to which reference is made for details of the method.

The large pore zeolites which are useful as catalysts in the process of this invention, i.e., those zeolites having a Constraint Index of no greater than about 2, are well known to the art. Representative of these zeolites are zeolite Beta, zeolite X, zeolite L, zeolite Y, ultrastable zeolite Y (USY), dealuminized Y (Deal Y), rare earth-exchanged zeolite Y (REY), rare earth-exchanged dealuminized Y (RE Deal Y), mordenite, ZSM-3, ZSM-4, ZSM-12, ZSM-20, and ZSM-50 and mixtures of any of the foregoing.

Zeolite Beta is described in U.S. Reissue Pat. No. 28,341 (of original U.S. Pat. No. 3,308,069), to which reference is made for details of this catalyst.

Zeolite X is described in U.S. Pat. No. 2,882,244, to which reference is made for the details of this catalyst.

Zeolite L is described in U.S. Pat. No. 3,216,789, to which reference is made for the details of this catalyst.

Zeolite Y is described in U.S. Pat. No. 3,130,007, to which reference is made for details of this catalyst.

Low sodium ultrastable zeolite Y (USY) is described in U.S. Pat. Nos. 3,293,192; 3,354,077; 3,375,065; 3,402,996,; 3,449,070; and 3,595,611, to which reference is made for details of this catalyst.

Dealuminized zeolite Y (Deal Y) can be prepared by the method found in U.S. Pat. No. 3,442,795, to which reference is made for details of this catalyst.

Zeolite ZSM-3 is described in U.S. Pat. No. 3,415,736, to which reference is made for details of this catalyst.

Zeolite ZSM-4 is described in U.S. Pat. No. 3,923,639, to which reference is made for details of this catalyst.

Zeolite ZSM-12 is described in U.S. Pat. No. 3,832,449, to which reference is made for the details of this catalyst.

Zeolite ZSM-20 is described in U.S. Pat. No. 3,972,983, to which reference is made for the details of this catalyst.

Zeolite ZSM-50 is described in U.S. Pat. No. 4,640,829, to which reference is made for details of this catalyst.

Included within the definition of the useful zeolites are crystalline porous silicoaluminophosphates such as those disclosed in U.S. Pat. No. 4,440,871, the catalytic behavior of which is similar to that of the aluminosilicate zeolites.

Aromatic compounds which can be alkylated according to the process of the invention comprise mononuclear and polynuclear aromatics such as benzene, naphthalene, anthracene, phenanthracene, substituted and unsubstituted. Substituent groups include halide, alkyl, alkenyl, alkynyl, alkoxy, alkoxo, amino, acetamido, carbamoyl, hydroxy, and mercapto. These aromatic compounds can be alkylated with pyrolyzed plastic neat, in solution or as a component part of a complex mixture such as a petroleum refinery stream. Petroleum refinery streams of particular utility as feedstreams for aromatics alkylation according to the process of the invention include the crackate from catalytic or thermal cracking processes, reformate, lube raffinate and extract, light cycle oil (LCO), light and heavy gas oil and straight run gasoline.

The alkylation can be either performed with pre-degraded plastics or conducted in-situ with thermal/catalytic degration of the plastic.

The pyrolyzed plastics used in this invention were obtained from the joint-industry experimental program on plastics pyrolysis. Table 1 and Table 2 provide the physical properties and compositional analysis of the pyrolyzed plastics.

TABLE 1

| Properties of Pyrolyzed Plastics | |
|---|---|
| Specific Gravity | 0.8617 |
| Pour Point | 15 F |
| Viscosity @ 75° F. | 1.266 cst |
| Viscosity @ 122° F. | 1.083 cst |
| Sulfur | 460 ppm |
| Nitrogen | 85 ppm |
| Chlorine | 8 ppm |
| Metals | |
| Al | <5 ppm |
| Ca | 29 ppm |
| Mg | 2.5 ppm |
| Zn | 7.5 ppm |
| Na | <1.5 ppm |
| Fe | <1 ppm |

TABLE 2

Compositional Analysis of Pyrolyzed Plastics

Yield of 500–° F. Plastics: 64 wt %

| | 500–° F. | 500+° F. | Total |
|---|---|---|---|
| Aromatics, wt % | 78.5 | 37.5 | 63.8 |
| Olefins, wt % | 18.44 | 7.3 | 28.8 |
| Paraffins, wt % | 0.2 | 3.4 | 1.3 |
| Naphthenes, wt % | 2.9 | 11.8 | 6.1 |

While the 500–° F. cut of the pyrolyzed plastics primarily contains the aromatic olefins (styrene), the 500+° F. cut contains the aliphatic olefins. Carbon number of the olefins in the plastics is 14.

The alkylation process of the invention is illustrated in the following examples.

EXAMPLE 1

Alkylation of Methyl Naphthalene with 500+° F. Pyrolyzed Plastics

Alkylated naphthalene is used as solubilizer in automatic transmission fluid (ATF). This example illustrates the alkylation of a model two-ring aromatic, methyl naphthalene, in the presence of WOx/ZrO2, USY (ultra-stable Y) and MCM-56 catalysts with the 500+° F. fraction of the pyrolyzed plastics at 400° F. for 6 hours. Feed aromatic to olefin ratio was 3 to 1 while the weight ratio of the feed to the catalyst was 10 to 1. The 500+ F. fraction of the pyrolyzed plastics has been depleted of styrene which is primarily in the 500–° F. fraction of the pyrolyzed plastics.

Supercritical Fluid Chromatography (SFC) of the alkylation product indicates alkylation of the methyl naphthalene with the olefins in the pyrolyzed plastics. Detailed analysis of feed and product with olefin conversion to alkylated aromatics is given below in Table 3 for the three catalysts. 0.1 gram of the respective catalyst was used under the conditions described.

TABLE 3

| | Methyl Napth/ Plastics Feed | MCM-56 Product | USY Product | WOx/ ZrO$_2$ Product |
|---|---|---|---|---|
| Paraffins, wt % | 3.0 | 3.2 | 3.7 | 3.1 |
| Naphthenes, wt | 0.9 | 0.9 | 1.3 | 0.9 |
| Olefins/Olig, wt % | 11.8 | 5.8 | 6.4. | 7.5 |
| Other Arom, wt. % | 9.4 | 18.5 | 18.7 | 14.6 |
| Methyl Napth, wt. % | 75.0 | 71.7 | 70.0 | 73.9 |
| % Olefin Conv.(approx) to Alkylated Aromatics | 50 | 45 | 35 | |

EXAMPLE 2

Methyl Naphthalene Alkylation with TLP from Pyrolyzed Plastics

This example illustrates the alkylation of a model two-ring aromatic, methyl naphthalene in the presence of MCM-56, USY, WOx/ZrO2 and acidified clay with the total liquid product (TLP) of pyrolyzed plastics (3:1 methyl naphthalene/plastics mole ratio) at 400 F for 6 hours at a weight ratio of 1 to 0.1 of feed to catalyst.

The feed and product were analyzed by Field Ionization Mass Spectroscopy (FIMS). FIMS is a soft ionization technique that produces primarily molecular ions. From the profiles of the molecular ions shifts in molecular weight can be determined and, depending on sample complexity, determine which classes of compounds are undergoing reactions. FIMS analysis of the alkylation reaction products for each catalyst shows alkylation of methyl naphthalene with styrene and other olefins with methyl naphthalene alkylated with styrene being the primary reaction product. The FIMS analysis indicates olefin conversion with the model compound feed wherein the product is a mixture of alkylated methyl naphthalene and olefin oligomers. Alkylation of the methyl naphthalene results in a molecular weight shift of the heavy olefin envelope to the right as a result of alkylation and oligomerization.

The FIMS results show that the molecular weight shift with MCM-56 is greater than that of USY. The double envelope in the FIMS spectrum of the reaction product is due to monoaromatic and diaromatic alkylation respectively with the olefins in the plastics. The alkylation of two aromatic molecules with one olefin molecule allows more efficient utilization of the olefin and also permits the formation of molecules with unique lube properties.

EXAMPLE 3

Alkylation of Toluene with 500+° F. Pyrolyzed Plastics

This example illustrates the alkylation of a model one-ring aromatic, toluene, in the presence of acidified clay, USY (ultra-stable Y) and MCM-56 with the 500+° F. cut of pyrolyzed-plastics at 400° F. for 6 hours. FIMS spectra was obtained of the reaction products from processing 1 g of the feed over 0.1 g of acidified clay, USY and MCM-56 respectively. As with methyl naphthalene, FIMS analysis indicates aromatic alkylation/olefin oligomerization with alkylated toluene being the primary reaction product. Alkylation over all three catalysts results in a shift in the molecular weight envelope to the right as a result of toluene alkylation with the heavy olefins in the plastics. FIMS spectra over both USY and MCM-56 indicate the double molecular envelopes resulting from monoaromatic and diaromatic alkylation with the heavy olefins which is similar to the behavior displayed by methyl naphthalene in Example 1.

EXAMPLE 4

Alkylation of Toluene with the TLP from Pyrolyzed Plastics

This example illustrates the alkylation of a model one-ring aromatic, toluene, in the presence of USY (ultra-stable Y) and MCM-56 with pyrolyzed whole plastics at 400° F. for 6 hours. FIMS spectra of the reaction product was obtained from processing 1 g of this feed over 0.1 g of MCM-56 and USY respectively. As with methyl naphthalene, FIMS analysis indicates toluene alkylation/ olefin oligomerization with toluene alkylated and styrene being the primary reaction product.

For all the cases involving alkylation of model compounds with pyrolyzed plastics, FIMS analysis shows that the rate of reaction is roughly in the order MCM-56>USY. Both WOx/ZrO2 and acidified clay result in lower olefin conversion than MCM-56 or USY.

EXAMPLE 5

Alkylation of Lube Extract with TLP from the Pyrolyzed Plastics

This example illustrates the alkylation of a lube extract from a furfural-refined Arab Light 483 having the properties depicted in Table 4. The feed was the entire pyrolyzed plastics and the reaction was carried out over USY (ultra-stable Y) and MCM-56, respectively. The alkylation reaction was conducted in a 1 liter autoclave using 125 g (0.42 moles) of lube extract and 25 g (0. 1 78 moles) of pyrolyzed plastics (2.4:1 mole ratio of aromatic/olefin) with 15 g of catalyst for 8 hours at 400° F. under a nitrogen pressure of 400 psig. After decanting and filtering the catalyst, the total liquid product was vacuum distilled at 650° F. to obtain lube range material. The conversion of 650–° F. material in the feed to 650+° F. lube range material is detailed in Table 5.

TABLE 4

Properties of Arab Light 483 Extract

| | |
|---|---|
| kv 40° C. | 5.194 cS |
| kv 100° C. | 49.650 cS |
| Sulfur | 5.2 wt % |
| Nitrogen | 1500 ppm |
| Simulated Distillation (°F.) | |
| IBP 568.5, 10% 653.6, 30% 701.1, 50% 739.9, FBP 805.8 | |

TABLE 5

650+° F. Yield in Furf Extract/Plastics Feed: 77.5%

| | MCM-56 | USY |
|---|---|---|
| % 650+° F. Yield | 82 | 81 |
| % Shift in 650+° F. Yield | 4.5 | 3.5 |
| % 650–° F. Incorporated to 650+° F. | ~20 | ~15 |

Based on compositional analysis of the products generated by alkylation of the model compound methyl naphthalene with the pyrolyzed plastics, the increase in lube yield with the furfural extracts is considered to be due to aromatics alkylation, which should lower the mutagenicity index of the lube extract and upgrade it to a higher value product.

EXAMPLE 6

Alkylation of Hydrotreated Light Cycle Oil

This example illustrates the alkylation of a hydrotreated light cycle oil (LCO) with the total liquid product from the pyrolyzed plastics over MCM-56. The alkylation reaction was carried out in a 1 liter autoclave using 103.6 g (0.66 moles, MW=158) of hydrotreated LCO and 46.5 g (0.33 moles) of pyrolyzed plastics (2:1 mole ratio of LCO/plastic) with 10 g of catalyst for 6 hours at 400° F. at 400 psig. The liquid product was then vacuum distilled at 650° F. to obtain distillate and lube range fractions. The cetane index of the distillate fraction was 32 compared to 29 for the hydrotreated LCO feed. The cetane increase is considered to be due to aromatic alkylation.

Alkylation of mono and polynuclear aromatics is a key processing step in the chemical, fuels and lube components of the petroleum industry. Alkylation of lube extracts is one possible way to lower their mutagenicity index, thereby upgrading a low value refinery stream to higher value products such as printing inks, aromatic oils, plasticizers, rubber extenders or even lube basestock. Alkylation of LCO is a potential way to improve its cetane index for use as diesel fuel. Alkylated aromatics such as naphthalene are produced as solubilizers in automatic transmission fluid (ATF) while linear alkyl benzenes (LABS) find application in the detergent business. The use of thermally or catalytically degraded plastics for the alkylation of aromatics provides a lower cost alternative to existing olefin sources and simultaneously offers a safe, environmentally friendly method to recycle scrap plastics to useful products.

What is claimed is:

1. A process for the production of alkylaromatic compounds employing olefins contained in an olefinic liquid comprising the total liquid product from thermally or catalytically cracked plastics as alkylating agent, said process comprising:

contacting a feedstream comprising alkylatable aromatics and said total liquid product with acidic alkylation catalyst under alkylation conditions in an alkylation zone; and recovering an effluent stream comprising said alkylaromatic compounds.

2. The process of claim 1 wherein said olefinic liquid comprises said cracked plastics having a boiling point of 500+° F.

3. The process of claim 1 wherein said olefinic liquid comprises said cracked plastics having a boiling point of 500–° F.

4. The process of claim 1 wherein said alkylatable aromatics comprise mononuclear or polynuclear aromatics.

5. The process of claim 4 wherein said mononuclear or polynuclear aromatics contain one or more substituents selected from the group consisting of halide, alkyl, alkenyl, alkynyl, alkoxy, amino, carboxamido, hydroxy, alkyloxo, sulfoxy and mercapto.

6. The process of claim 1 wherein said alkylation catalyst is selected from Lewis acids.

7. The process of claim 6 wherein said Lewis acids are selected from the group consisting of HF, $H_2SO_4$, $AlCl_3$, $BF_3$, $FeCl_3$, $TiCl_4$, $ZnCl_2$ and $P_2O_5$.

8. The process of claim 1 wherein said catalyst is selected from acidic layered clays, acidic natural or synthetic zeolites and mixed metal oxide super acids.

9. The process of claim 8 wherein said zeolites are selected from the group consisting of ZSM-5, ZSM-11, ZSM-12, ZSM-23, ZSM-35, and ZSM-48, ZSM-50, Zeolite Beta, MCM-56, MCM-22, MCM-36, MCM-49, MCM-56, ultrastable zeolite Y (USY), zeolite X, TMA Offretite, TEA Mordenite, Clinoptilolite, Mordenite, rare earth-exchanged zeolite Y (REY), Amorphous Silica-Alumina and Dealuminized Y.

10. The process of claim 1 wherein said alkylatable aromatics comprise alkylatable aromatics in a petroleum refinery stream.

11. The process of claim 10 wherein said petroleum refinery stream comprises lube oil raffinate or extract.

12. The process of claim 10 wherein said petroleum refinery stream comprises catalytic or thermal crackate.

13. The process of claim 10 wherein said petroleum refinery stream comprises light cycle oil.

14. The process of claim 1 wherein said alkylation conditions comprise temperature between 50° F. and 1,000° F., pressure between atmospheric and 7,000 kPa.

15. The process of claim 1 wherein the ratio of alkylatable aromatics to said olefins in the feedstream is between 0.1 to 1 and 20 to 1.

16. The process of claim 15 wherein the ratio is about 3 to 1.

17. The process of claim 1 wherein said zone is a fixed or fluidized catalyst bed reactor.

18. The process of claim 1 wherein said cracked plastics are selected from the group consisting of high density polyethylene, polypropylene and polystyrene.

* * * * *